United States Patent [19]

Feuer et al.

[11] 4,218,404
[45] * Aug. 19, 1980

[54] ω-AMINOCARBOXYLIC ACID AMIDES

[75] Inventors: László Feuer; Arpad Furka; Ferenc Sebestyen; Anikó Horváth; Jolán Hercsel, nee Szepespataki, all of Budapest, Hungary

[73] Assignee: Chinoin Gyógyszer és Vegyészeti Termekék Gyára Rt., Budapest, Hungary

[*] Notice: The portion of the term of this patent subsequent to Jul. 25, 1995, has been disclaimed.

[21] Appl. No.: 884,640

[22] Filed: Mar. 8, 1978

Related U.S. Application Data

[63] Continuation-in-part of Ser. No. 792,917, May 2, 1977, Pat. No. 4,102,948.

[30] Foreign Application Priority Data

May 6, 1976 [HU] Hungary .............................. CI 1662

[51] Int. Cl.² ........................ A61K 31/66; C07F 9/09; C07C 143/15; C07C 143/53
[52] U.S. Cl. ............................. 260/944; 260/507 R; 260/513 N; 424/211; 424/315
[58] Field of Search ............... 260/944, 507 R, 513 N, 260/987

[56] References Cited

U.S. PATENT DOCUMENTS

| 1,485,377 | 3/1924 | Engels ................................. 260/987 |
| 4,102,948 | 7/1978 | Feuer et al. .......................... 260/944 |

FOREIGN PATENT DOCUMENTS 1954090  5/1971  Fed. Rep. of Germany ...... 260/513 N

OTHER PUBLICATIONS

Schroder et al., "The Peptides," vol. 1, 1965, p. 26.

Primary Examiner—Anton H. Sutto
Attorney, Agent, or Firm—Karl F. Ross

[57] ABSTRACT

The invention relates to novel ω-aminocarboxylic acid amides having the formula (I)

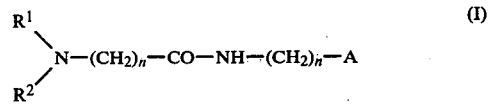

wherein
A is —SO₂OH or —OPO(OH)₂,
R¹ is hydrogen, an acyl group, such as benzoyl, arylsulfonyl, alkoxycarbonyl, cycloalkoxycarbonyl or aralkoxycarbonyl group or an aralkoxycarbonyl group having a halogen, alkoxy, nitro, phenylazo or alkoxyphenylazo substituent, alkyl-substituted aryloxycarbonyl or carbonyl,
R² is hydrogen or a carbonyl group, with the proviso that when R¹ and R² each stand for carbonyl, the two carbonyl groups form a ring through an intervening o-phenylene, alkylene or vinylene group when A is —SO₂OH and R¹ is an acyl group such as benzoyl, aryl sulfonyl, alkoxy-carbonyl, cycloalkoxycarbonyl or aryloxycarbonyl group or an aralkoxy carbonyl group having a halogen, alkoxy, nitro, phenylozo or alkoxyphenylazo substituent or an alkyl-substituted aryloxycarbonyl group or carbonyl group,
R² is hydrogen or a carbonyl group, with the proviso that when R¹ and R² each stand for carbonyl, the two carbonyl groups form a ring through an intervening o-phenylene, alkylene or vinylene group when A is —O—P—O(OH)₂ and n is equal to 2 or 3, and salts of the above compounds, furthermore to a process for the preparation thereof.

The novel compounds according to the invention possess valuable pharmacological effects in reducing blood sugar levels or can be applied as intermediate in the synthesis of biologically active compounds.

13 Claims, No Drawings

ω-AMINOCARBOXYLIC ACID AMIDES

This application is a continuation-in-part of Ser. No. 792,917, filed May 2, 1977, now U.S. Pat. No. 4,102,948, issued July 27, 1978.

This invention relates to novel ω-aminocarboxylic acid amides having formula (I)

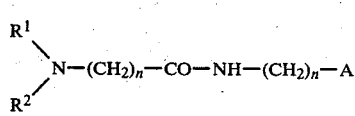

wherein

A is a group of the formula —SO$_2$OH or —OPO(OH)$_2$,

R$^1$ is hydrogen, an acyl group, such as benzoyl, arylsulfonyl, alkoxycarbonyl, cycloalkoxycarbonyl or aralkoxycarbonyl group or an aralkoxycarbonyl group having a halogen, alkoxy, nitro, phenylazo or alkoxyphenylazo substituent, an alkyl-substituted aryloxycarbonyl group or a carbonyl group, R$^2$ is hydrogen or a carbonyl group, with the proviso that when R$^1$ and R$^2$ each stand for carbonyl, the two carbonyl groups form a ring through an intervening o-phenylene, alkylene or vinylene group, when A is —SO$_2$OH and R$^1$ is an acyl group such as benzoyl, arylsulfonyl, alkoxycarbonyl, cycloalkoxycarbonyl or aryloxycarbonyl group or an aralkoxy carbonyl group having a halogen, alkoxy, nitro, phenylazo or alkoxyphenylazo substituent or an alkyl- substituted aryloxycarbonyl group or carbonyl group, R$^2$ is hydrogen or a carbonyl group, with the proviso that when R$^1$ and R$^2$ each stand for carbonyl, the two carbonyl groups form a ring through an intervening o-phenylene, alkylene or vinylene group when A is —O—P—O(OH)$_2$ and n is equal to 2 or 3, and salts of the above compounds. The application also discloses a process for the preparation of such ω-aminocarboxylic acid amides.

The novel compounds according to the invention possess valuable therapeutic effects or can be used as intermediates in the synthesis of compounds with valuable biological or pharmacological activities.

With respect to their pharmacological activities, γ-aminobutyryl-taurine and γ-amino-butyryl-ethanolamine phosphate and their salts are particularly interesting representatives of the novel compounds according to the invention. These substances, even when administered in very low concentrations (micrograms per kg body weight), significantly decrease the blood sugar level of rats, increase the vitamin A level of the serum, and enhance the incorporation of labelled sulfate ions into the lung tissues of chicken embryos.

A common structural characteristic of the novel compounds having formula (I) is that they are amido derivatives of β- or γ-aminocarboxylic acids having optionally a substituent on the amino group, wherein the alkyl side chain of the amide-forming primary alkylamine moiety contains a strongly acidic group in position β or γ.

The new compounds according to the invention can be prepared far more simply and easily than the structurally related α-amino-dicarboxylic acid amides, since in this instance, the carboxy group in position α need not be protected.

The novel compounds of the formula (I) and their salts can be prepared according to the invention as follows:

(a) when a compound of the general formula (I) containing an unsubstituted primary amino group is to be prepared, the R$^3$ and/or R$^4$ protecting groups of a compound of formula (II),

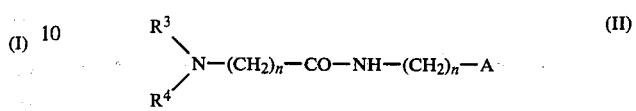

wherein n and A are as defined above and

R$^3$ represents an aralkyl, formyl, trifluoroacetyl, p-toluene-sulfonyl or carbonyl group or a group of the formula R$^{12}$—O—CO— (wherein R$^{12}$ is a C$_{1-4}$ alkyl, cycloalkyl, aralkyl, substituted aralkyl, aryl or substituted aryl group) and R$^4$ is hydrogen or a carbonyl group, with the proviso that when R$^3$ and R$^4$ each stand for carbonyl, the two carbonyl groups form a ring through an intervening o-phenylene group, are split off by acidolysis, hydrogenolysis, treatment with a dilute ammonium hydroxide solution, treatment with sodium amide or treatment with hydrazine; or (b) a compound of formula (III),

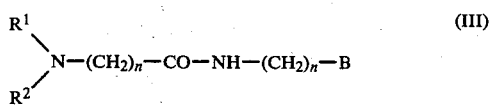

wherein

R$^1$, R$^2$ and n are as defined above and

B is (i) an —SH, —SOOH or —OH group, or (ii) a group of formula —SO$_2$R$^{10}$, wherein R$^{10}$ is a C$_{1-4}$ alkoxy or aralkoxy group, or (iii) a group of formula —S—S—R$^{11}$, wherein R$^{11}$ is a C$_{1-4}$ alkyl, aralkyl or aryl group or a group of the formula (R$^1$, R$^2$)N—(CH$_2$)$_n$—CO—NH—(CH$_2$)$_n$—, is oxidized or hydrolyzed, or reacted with an alkali metal or alkali hydrogen sulfite, or esterified with phosphoric acid; or (c) when a compound of formula (I), wherein A is a sulfonic acid group, is to be prepared, a compound of formula (IV);

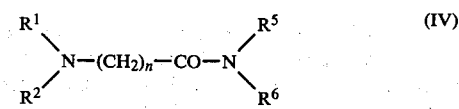

wherein R$^1$, R$^2$ and n are as defined above, R$^5$ is hydrogen or methylene group and R$^6$ is an alkali metal ion, vinyl group or methylene group, with the proviso that when R$^5$ and R$^6$ each stand for methylene, the two methylene groups together form an aziridine ring, is alkylated with an alkali metal salt of a haloalkylsulfonic acid or is reacted with sodium hydrosulfite or sodium sulfite; or (d) when a compound of formula (I), wherein A is a sulfonic acid group, is to be prepared, a compound of the formula (V),

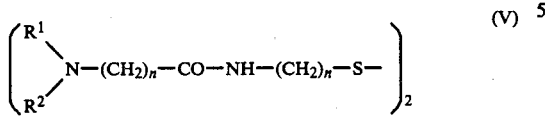

wherein $R^1$, $R^2$ and n are as defined above, is oxidized; or (e) when a compound of formula (I) containing an unsubstituted primary amino group is to be prepared, a compound of formula (VI),

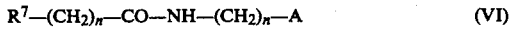

$$R^7-(CH_2)_n-CO-NH-(CH_2)_n-A \quad (VI)$$

wherein n and A are as defined above and $R^7$ stands for halogen, nitro, hydrazino, hydroxylamino, p-toluenesulfonyloxy, arylazo, substituted arylazo, monoarylhydrazino or diarylhydrazino group, is reduced or reacted with ammonia; or (f) when a compound of formula (I) containing an unsubstituted primary amino group is to be prepared, a compound of formula (VII),

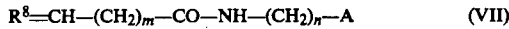

$$R^8=CH-(CH_2)_m-CO-NH-(CH_2)_n-A \quad (VII)$$

wherein n and A are as defined above, m is equal to 1 or 2, and $R^8$ is oxygen, an oximino group, an imino group or a group of formula $=N-NH-R^{13}$, and in this latter formula $R^{13}$ stands for hydrogen or an aryl group, is reduced or reacted with ammonia and potassium cyanide, and the resulting compound is hydrogenated, or it is reacted with α-methyl-benzylamine and the resulting compound is hydrogenated; or (g) a compound of formula (VIII),

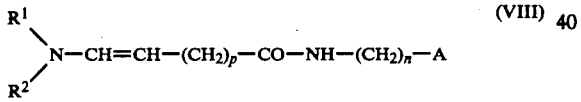

wherein $R^1$, $R^2$, n and A are as defined above and p is equal to zero or one, is hydrogenated; or (h) when a compound of formula (I) containing γ-aminobutyric acid units is to be prepared, a compound of the formula (IX),

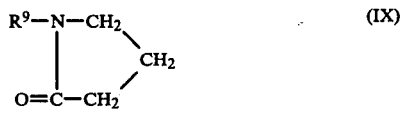

wherein $R^9$ is hydrogen, a $C_{1-4}$ alkyl, aryl, substituted aryl, aralkyl, acyl, arylsulfonyl group or a group of the formula $R^{12}-O-CO-$, and in this latter formula $R^{12}$ stands for a $C_{1-4}$ alkyl, cycloalkyl, aralkyl, substituted aralkyl, aryl or substituted aryl group, is reacted with a compound of formula (X)

$$H_2N-(CH_2)_n-A \quad (X)$$

wherein n and A are as defined above, or with a salt of this latter compound; or (i) when a compound of formula (I) containing an unsubstituted primary amino group and having a sulfonic acid group in the place of A is to be prepared, a compound of formula (XI),

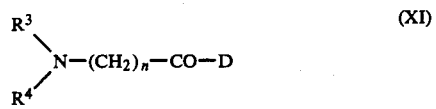

wherein $R^3$, $R^4$ and n are as defined above D stands for hydroxy, azido, succinimidoxy, p-nitrophenoxy, pentachlorophenoxy or a $C_{2-4}$ alkoxycarbonyloxy group, is reacted with a compound of formula (XII),

$$[H_2N-(CH_2)-S-]_2 \quad (XII)$$

wherein n is as defined above, the resulting product is oxidized, and the protecting groups attached to the amino groups of the resulting compound are split off as discussed in method (a) above; or (j) when a compound of formula (I) containing an unsubstituted primary amino group is to be prepared, a compound of formula (XI), wherein $R^3$, $R^4$, n and D are as defined above, is reacted with a compound of formula (X), wherein n and A are as defined above, and the protecting groups attached to the amino group of the resulting compound are split off as discussed in method (a) above; or (k) when a compound of formula (I) containing a protecting group on the amino group is to be prepared, a compound of the formula (XIII),

$$H_2N-(CH_2)_n-CO-NH-(CH_2)_n-A \quad (XIII),$$

wherein n and A are as defined above, is acylated; and, if desired, a compound of formula (I) is converted into its salt, or a salt of a compound having formula (I) is converted into the free base.

Of the above process variants, method (j) will be discussed first in detail. According to this method the compounds of formula (I) are prepared by forming an acid amide bond. In this instance a derivative of a β- or γ-aminocarboxylic acid having a protecting group on the amino moiety is coupled e.g. to 2-amino-ethanesulfonic acid (taurine), 3-amino-propane-sulfonic acid, 2-phosphoethanolamine or 3-phosphopropanolamine, respectively. Various groups can be used to block the free amino group of the starting aminocarboxylic acids. The most appropriate method of forming the amido bond is the so-called "activated ester method" (see E. Schröder and K. Lübke: The Peptides, Vol. 1; Methods of Peptide Synthesis, Academic Press, 1965).

Process variant (i) can be performed by acylating cystamine with a β- or γ-aminocarboxylic acid derivative. Various coupling methods, e.g. the activated ester method or the mixed anhydride method, can be used to form the acid amide bond. The resulting compound is then reacted with hydrogen peroxide or a peracid for the oxidative splitting of the disulfide bond (see also method d). In this latter step compounds of formula (I) are obtained.

According to method (b) first a β- or γ-aminocarboxylic acid amide containing another functional group in the place of the strongly acidic terminal group is prepared. When this functional group is a sulfhydryl group or a sulfinic acid residue, the desired compounds can be prepared by subjecting the intermediate to oxidation. The intermediates, containing a halogen atom as functional groups, can be reacted with an alkali metal sulfite or alkali metal bisulfite to form the respective compounds of formula (I), wherein A is a sulfonic acid residue. The hydroxy-containing intermediates can be esterified to form the corresponding dihydrophosphate derivatives of formula (I). Finally, the intermediate containing a sulfonic ester group as functional group can be converted into the corresponding compounds of formula (I) by mild partial hydrolysis.

When a β- or γ-aminocarboxylic acid amide containing a protected amino group is used as the starting substance, the compounds of formula (I) can be prepared according to process variant (c) by reacting this compound at one of the amide hydrogens of acidic character with an alkali metal reactant, such as metallic sodium, and treating the resulting alkali metal derivative e.g. with 2-bromo-ethanesulfonic acid or a salt thereof. Method (c) is also useful for the conversion of vinylamides of β- or γ-aminocarboxylic acids, furthermore for the conversion of compounds containing an aziridine ring as the amine component. These compounds can be reacted with alkali metal sulfites or alkali metal bisulfites to form the desired compounds of formula (I).

According to methods (e) and (f), a carboxylic amide containing a substituent other than amino group in position β or γ is converted into the corresponding β- or γ-amino derivative. As starting compounds, amides of β- or γ-nitro-, arylazo-, hydrazo-, arylahydrazo-, hydroxylamino-, oximino- or iminocarboxylic acids, and amides of β- or γ-ketocarboxylic acid hydrazones can be utilized. These compounds can be converted into the desired end products of formula (I) by reduction, preferably by catalytic hydrogenation. When a β- or γ-halo- or β- or γ-(p-toluenesulfonyloxy)-carboxylic acid amide is the starting substance, the desired β- or γ-amino compounds of formula (I) can be prepared by amine substitution. The amino group can be introduced into the molecule by methods known per se. Similarly, the corresponding β- or γ-ketocarboxylic acid amides can be converted into the β- or γ-amino compounds of formula (I) by methods known per se, e.g. by reacting the keto derivatives with potassium cyanide in the presence of ammonium hydroxide and hydrogenating the resulting compound in the presence of cobalt chloride (Bull. Chem. Soc. Japan 36, 763 (1963)).

When a compound containing a double bond in the β- or γ-aminocarboxylic acid moiety is used as the starting substance, this can be converted into the corresponding derivative of formula (I) by hydrogenation (see method g).

End products of formula (I) can also be prepared by method (h). In this instance when e.g. pyrrolid-1-one is reacted with taurine, homotaurine or another amine containing a strongly acidic functional group, or with an alkali metal or tertiary amine salt of the above compounds, the lactam ring splits off and a β- or γ-amide of formula (I) is formed.

Those compounds of formula (I), wherein a substituent is attached to the amino group, can be prepared when the corresponding unsubstituted amino derivatives. According to method (k), the free amino compounds are acylated in a manner known per se to form the corresponding acetyl, benzoyl, p-toluenesulfonyl, etc. compounds.

The pharmacological properties of the novel compounds according to this invention were investigated by the following tests:

Effects of γ-aminobutyryl-cholamine phosphate exerted on the blood sugar level

The tests were performed on groups each consisting of 20 rats. The blood sugar level values were measured after 18 hours of starvation. The compounds under study were administered for 4 days in the form of a solution in daily oral dosages of 1 μ/kg body weight. The following results were observed:
control: 106 mg%
γ-aminobutyryl-cholamine phosphate: 95 mg%
γ-aminobutyryl-taurine: 92 mg%
Significance level: $P<0.05$ for both cases.

Effects on the serum vitamin A level:

The tests were performed in male Wistar rats weighing 200 g. Groups each consisting of 20 rats were applied in the tests. The test period lasted 6 days. The results are summarized in Table 1.

Table 1

| Dosage μg/200 g body wt. | γ-aminobutyryl-choline phosphate Vitamin A level, μg | γ-aminobutyryl taurine Vitamin A level, μg |
|---|---|---|
| 0 | 9.0 | 9.0 |
| 5 | 11.5$^x$ | 11.5$^x$ |
| 1 | 12.5$^x$ | 11.0$^x$ |
| 0.3 | 13.5$^x$ | 12.0$^x$ |
| 0.1 | 16.6$^x$ | 15.5$^x$ |
| 0.05 | 15.2$^x$ | 14.4$^x$ |
| 0.01 | 14.8$^x$ | 14.5$^x$ |
| 0.005 | 14.8$^x$ | 14.5$^x$ |

$^x$Significance level: $P < 0.01$

Effects on blood silicon levels

The tests were performed on inbred male rabbits weighing 2.5 to 3 kg. The compound under study was administered orally to the animals in the daily dosages indicated in Table 2 below. The silicon content of the blood was determined according to the method of Gaubatz (Klin. Wschrft, 14, 1753, 1935) from blood samples, 5 ml in volume, taken from the ear vein. The results observed as summarized in Table 2.

Table 2

| | γ-aminobutyryl-cholamine phosphate | | | | | |
|---|---|---|---|---|---|---|
| | Silicon level, mg/ of blood | | | | | |
| Dosage | 0 hours | 5th day | 7th day | 13th day | 20th day | 40th day |
| 0 (control) | 0.100 ±0.005 | 0.098 ±0.011 | 0.120 ±0.017 | 0.122 ±0.016 | 0.130 ±0.011 | 0.153 ±0.016 |
| 5 μg/day | 0.090 ±0.003 | 0.156 ±0.010 | 0.154 ±0.006 | 0.184 ±0.005$^x$ | 0.305 ±0.010$^{xx}$ | 0.336 ±0.011$^{xx}$ |
| 10 μg/day | 0.105 ±0.005 | 0.174 ±0.004 | 0.170 ±0.004 | 0.200 ±0.011$^x$ | 0.368 ±0.115$^{xx}$ | 0.359 ±0.013$^{xx}$ |
| | γ-aminobutyryl taurine | | | | | |
| | Silicon level, mg/g of blood | | | | | |
| Dosage | 0 hours | 5th day | 7th day | 13th day | 20th day | 40th day |
| 0 /control | 0.110 ±0.006 | 0.100 ±0.010 | 0.130 ±0.015 | 0.134 ±0.012 | 0.150 ±0.010 | 0.160 ±0.021 |

Table 2-continued

| | | | | | | |
|---|---|---|---|---|---|---|
| 5 μg/day | 0.100 ±0.001 | 0.140 ±0.005 | 0.152 ±0.003 | 0.180 ±0.002+ | 0.310 ±0.008++ | 0.310 ±0.010++ |
| 10 μg/day | 0.100 ±0.004 | 0.164 ±0.004 | 0.156 ±0.004 | 0.195 ±0.010+ | 0.354 ±0.110++ | 0.350 ±0.013++ |

Significance levels:
$^x P < 0.01$
$^{xx} P < 0.001$

The results are significant on the $P < 0.01$ level from the 13th day on, and on the $P < 0.001$ level from the 20th day on.

Joint effects of the compounds of the invention with vitamin A in the implantation cotton granuloma test:

The tests were performed on male Sprague-Dawley rats weighing 110 to 120 g. The granuloma formation was tested according to the method of Lee et al. (Pharm. Sci. 62, 895 1973). The cotton tampons, implanted subcutaneously into the dorsolateral region, were removed after 10 days. The tampons were dried at 65° C. until constant weight and then weighed. The results are listed in Table 3.

Table 3

| Group No. | Vita-min A$^x$ local, mg | Active Agent local, μg | Active Agent oral, μg/day | Weight of the dry granuloma * mg$_p$ cholamine compound | mg** |
|---|---|---|---|---|---|
| I. (control) | — | — | — | 50 ± 1.3 | 51 ± 3.1 |
| II. (solvent) | — | — | — | 51 ± 3.0 | 53 ± 5.6 |
| III. | 2 | — | — | 62 ± 22.1 | 61 ± 6.1 |
| IV. | 2 | 0.1 | — | 63 ± 2.2 | 64 ± 6.2 |
| V. | — | — | 0.1 | 75 ± 2.4 | 74 ± 7.0 |
| VI. | 2 | — | 0.1 | 92 ± 4.0 | 91 ± 15.0 |

$^x$Produced by the firm Hoffmann La-Roche
*γ-aminobutyryl-cholamine phosphate
**γ-amino-butyryl-taurine The significance levels are as follows:
between groups II and III: $P < 0.05$
between groups II and V: $P < 0.001$ The process aspects of this invention are set forth in more detail by the aid of the following non-limiting Examples.

EXAMPLE 1

3.94 g (11 mmoles) of N-carbobenzoxy-γ-aminobutyric acid p-nitrophenylester (J. Org. Chem. 27, 684 1962) are dissolved in 75 ml of absolute pyridine, and the solution is cooled to 0° C. A solution of 1.25 g (10 mmoles) of taurine in 10 ml of water is added to the above solution under stirring and without further cooling, and then 1.4 ml (10 mmoles) of triethylamine are added. The reaction mixture is allowed to stand at room temperature for 72 hours, and then it is evaporated in vacuo at 35° C. The residue is dissolved in 10 ml of water, the solution is acidified with concentrated hydrochloric acid, and the acidic mixture is extracted in a continuous extractor for 8 hours with ether in order to remove p-nitro-phenol. The aqueous phase is evaporated in vacuo. The residue is dissolved in 10 ml of water, and the solution is poured onto a chromatographic column (20×2.2 cm) filled with Dowex 50×2 resin in the H+ form. The column is eluted with water. 150 ml of the effluent are collected. This solution, now free of triethylamine, is evaporated in vacuo at 35° C. The residue is dried in a desiccator over phosphorous pentoxide. 3.23 g (94%) of N-carbobenzoxy-γ-aminobutyryl-taurine are obtained.

EXAMPLE 2

1.30 g (5.5 mmoles) of N-carbobenzoxy-γ-aminobutyric acid (J. Org. Chem. 24, 863 1959) are dissolved in 20 ml of absolute acetonitrile. The solution is cooled to −15° C. under exclusion of atmospheric moisture, and then 0.77 ml (5.5 mmoles) of absolute triethylamine are added dropwise to the stirred mixture, followed by the dropwise addition of 0.77 ml (5.5 mmoles) of isobutyl chloroformate. The mixture is stirred at −15° C. for 40 minutes, thereafter 1.4 ml (10 mmoles) of triethylamine and finally 10 ml of cold absolute acetonitrile are added to the solution. The mixture is stirred at −15° C. for 2 hours, and then stirring is continued at room temperature for 4 hours. The mixture is evaporated in vacuo at 30° C. The residue is admixed with 10 ml of ice-cold water under cooling and stirring, and the obtained mixture is evaporated in vacuo at 35° C. The residue is admixed with 10 ml of water and 20 ml of ethyl acetate. The ethyl acetate phase is separated, washed successively with 15 ml of water, 2×15 ml of 5% aqueous sodium carbonate solution, 2×15 ml of water, 2×15 ml of 1 n hydrochloric acid and 2×15 ml of water, dried over anhydrous sodium sulfate, filtered, and evaporated to dryness in vacuo at 30° C. The residue is dissolved in 5 ml of glacial acetic acid, and a freshly prepared mixture of 5 ml of 30% hydrogen peroxide and 15 ml of glacial acetic acid is added dropwise to the solution under cooling with ice. When the addition is over, the cooling bath is removed, the mixture is stirred at room temperature for 2 hours, and evaporated in vacuo at 30° C. The oily residue is dried in a desiccator first over phosphorous pentoxide and then over solid potassium hydroxide. 1.41 g (82%) of N-carbobenzoxy-γ-aminobutyryl-taurine are obtained.

EXAMPLE 3

The N-carbobenzoxy-γ-aminobutyryl-taurine obtained as described in Example 2 is dissolved in 10 ml of water. 100 mg of 10% palladium-on-carbon catalyst are added to the solution, and the mixture is hydrogenated for 2 hours. The catalyst is filtered off, and the filtrate is evaporated in vacuo at 35° C. The obtained crude product is crystallized from a 1:10 mixture of water and acetone. 0.798 g (76%) of γ-aminobutyryl-taurine are obtained: m.p.: 247° C.

Characteristic bands of the IR absorption spectrum (KBr): 3350 (amine=NH), 3200–2500 ($NH_3^+$), 1647 (amide=CO), 1550 (=NH), 1175, 1041, 550 ($SO_3^-$) $cm^{-1}$.

Analysis: Calculated for $C_6H_{14}N_2O_4S$ (210.26): C: 34.27%, H: 6.71%, N: 13.32%, S: 15.25%. Found: C: 34.30%, H: 7.10%, N: 12.83%, S: 14.90%.

EXAMPLE 4

10 ml of glacial acetic acid and 15 ml of a 3.3 molar hydrogen bromide solution in glacial acetic acid are added to 3.23 g of N-carbobenzoxy-γ-aminobutyryl-taurine, prepared as described in Example 1. The mixture is allowed to stand at room temperature for 2 hours, and then evaporated in vacuo at 35° C. The oily residue is triturated several times with ether, and the ether phase is decanted. The residue is dried in a desiccator over solid potassium hydroxide. The obtained oily residue is dissolved in 2 ml of water and crystallized by the addition of 20 ml of acetone. The crude product is recrystallized from a 1:10 mixture of water and acetone to obtain 1.89 g (90%, calculated for the starting taurine) of γ-aminobutyryl-taurine.

EXAMPLE 5

1.9 g (5.5 mmoles) of N-carbobenzoxy-β-alanine-p-nitrophenyl ester (Biochemistry 4, 1884 1965) are reacted with 0.63 g (5 mmoles) of taurine as described in Example 1 to obtain 1.35 g (82%) of N-carbobenzoxy-β-alanyl-taurine.

EXAMPLE 6

The protecting group of 1.35 g of N-carbobenzoxy-β-alanyl-taurine, the product of Example 5, is split off as described in Example 4. The crude product is recrystallized from a 1:9 mixture of water and acetone to obtain 0.745 g (76%, calculated for the starting taurine) of β-alanyl-taurine M.p: 207°–209° C.

Characteristic bands appearing in the IR absorption spectrum (KBr): 3315, 3300 (amide=NH), 3200–2600 ($NH_3^+$), 1683, 1648 (amide=CO), 1648 ($NH_3^+$), 1563, 1540 (amide=NH), 1185, 1034, 540, 535 ($-SO_3^-$) $cm^{-1}$.

EXAMPLE 7

The protecting group of 1.35 g of N-carbobenzoxy-β-alanyl-taurine, the product of Example 5, is split off as described in Example 3. The crude product is recrystallized from a 1:9 mixture of water and acetone or from 80% aqueous ethanol to obtain 0.785 g (80%) of β-alanyl-taurine.

EXAMPLE 8

1.9 g (5.5 mmoles) of N-carbobenzoxy-β-alanine-p-nitro-phenyl ester are reacted with 696 mg (5 mmoles) of homotaurine as described in Example 1 to obtain 1.38 g (80%) of N-carbobenzoxy-β-alanyl-homotaurine.

EXAMPLE 9

The protecting group of 1.38 g of N-carbobenzoxy-β-alanyl-homotaurine is split off with hydrogen bromide in glacial acetic acid as described in Example 4. The crude product is recrystallized from a 1:9 mixture of water and acetone or from 80% aqueous ethanol to obtain 0.75 g (71%) of β-alanyl-homotaurine; m.p.: 205°–207° C.

Characteristic bands appearing in the IR absorption spectrum (KBr): 3338, 3305 (amide=NH), 3200–2600 ($NH_3^+$), 1681, 1669 (amide=CO), 1638 ($NH_3^+$), 1538, 1545, 1565 (amide=NH), 1190, 1043, 530 ($-SO_3^-$) $cm^{-1}$.

EXAMPLE 10

The protecting group of 1.38 g of N-carbobenzoxy-β-alanyl-homotaurine is split off by catalytic hydrogenation as described in Example 3 to obtain 0.808 g (77%) of β-alanyl-homotaurine.

EXAMPLE 11

3.94 g (11 mmoles) of N-carbobenzoxy-aminobutyric acid p-nitrophenyl ester are dissolved in 60 ml of absolute pyridine. The solution is cooled to 0° C., then the cooling bath is removed, and a solution of 1.41 g (10 mmoles) of ethanolamine phosphate in 20 ml of water is added dropwise to the stirred mixture. Thereafter 2.8 ml (20 mmoles) of triethylamine are added to the solution, and the mixture is allowed to stand at room temperature for 72 hours. The solution is evaporated in vacuo at 35° C. The oily residue is diluted with 10 ml of water, the aqueous solution is acidified with concentrated hydrochloride acid, and the acidic mixture is extracted continuously with ether for 8 hours. The aqueous phase is evaporated in vacuo. The oily residue is dissolved in 20 ml of distilled water, and the solution is poured onto a chromatographic column (36×2.2 cm) filled with Dowex 50×2 resin in the $H^+$ form. The column is eluted with distilled water. 250 ml of effluent are collected, and the solution is evaporated in vacuo at 35° C. The residue is dried in a desiccator over phosphorus pentoxide, and the obtained solid, white, hygroscopic substance is recrystallized from a 1:9 mixture of water and acetone. 3.13 g (87%) of N-carbobenzoxy-γ-aminobutyryl-ethanolamine phosphate are obtained; m.p.: 169°–171° C.

Characteristic bands appearing in the IR absorption spectrum (KBr): 3323 (amide=NH), 3500–2000 (P—OH), 1684 (carbobenzoxy —O—CO—NH—), 1642 (amide=CO), 1548 (amide=NH), 1080 (P=O in H-bond), 1283 (—C—O—P=O; phosphoric acid ester), 1050, 950 (P—O—alkyl) $cm^{-1}$.

EXAMPLE 12

The protecting group of 3.13 g of N-carbobenzoxy-γ-aminobutyryl-ethanolamine phosphate is split off as described in Example 4. The crude product is recrystallized from a 1:9 mixture of water and methanol to obtain 1.83 g (81%) of γ-aminobutyryl-ethanolamine phosphate; m.p.: 207° C.

Characteristic bands appearing in the IR absorption spectrum (KBr): 3295 (amide=NH), 3200–2000 ($NH_3^+OH^-$), 1642 (amide=CO), 1558 (amide=NH), 1145 (P=O in H-bond), 1045 (broad; asymmetric P—O—C—), 957 (symmetric P—O—C—) $cm^{-1}$.

Analysis: Calculated for $C_6H_{15}N_2O_5P$ (226.182): C: 31.86% H: 6.68% N: 12.39% P: 13.70%. Found: C: 31.50% H: 6.97% N: 12.04% P: 13.40%.

Additional compounds contemplated by the invention include the following:
N-acetyl-γ-aminobutyryl-taurine;
N-benzoyl-γ-aminobutyryl-taurine;
γ-aminobutyryl-homotaurine;
N-carbobenzoxy-γ-aminobutyryl-homotaurine;
N-acetyl-γ-aminobutyryl-ethanolamine phosphate;
N-benzoyl-γ-aminobutyryl-ethanolamine phosphate;
γ-aminobutyryl-propanolamine phosphate;
N-carbobenzoxy-γ-aminobutyryl-propanolamine phosphate;
β-alanyl-ethanolamine phosphate;
N-carbobenzoxy-β-alanyl-ethanolamine phosphate;
β-alanyl-propanolamine-phosphate; and
N-carbobenzoxy-β-alanyl-propanolamine phosphate; or a pharmaceutically acceptable salt thereof.

What we claim is:
1. A compound selected from the group consisting of:
N-acetyl-γ-aminobutyryl-taurine;
N-benzoyl-γ-aminobutyryl-taurine;
γ-aminobutyryl-homotaurine;
β-alanyl-homotaurine;
N-carbobenzoxy-γ-aminobutyryl-homotaurine;

N-carbobenzoxy-γ-aminobutyryl-ethanolamine phosphate;
N-carbobenzoxy-γ-aminobutyryl-propanolamine phosphate;
N-carbobenzoxy-β-alanyl-ethanolamine phosphate; and
N-carbobenzoxy-β-alanyl-propanolamine phosphate; or a pharmaceutically acceptable salt thereof.

2. A compound of the formula:

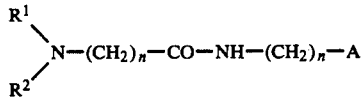

wherein
A is —OPO(OH)$_2$;
R$^1$ is carbobenzoxy;
R$^2$ is hydrogen; and
n is 2 or 3; or a pharmaceutically acceptable salt thereof.

3. A compound of the formula:

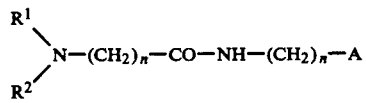

wherein
A is —SO$_2$OH;
n is 2 or 3;
R$^2$ is hydrogen; and
R$^1$ is acetyl or benzoyl; or of the formula:

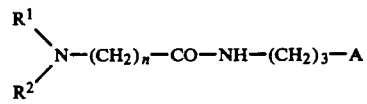

wherein
A is —SO$_2$OH;
n is 2 or 3;
R$^2$ is hydrogen; and
R$^1$ is hydrogen or carbobenzoxy; or a pharmaceutically acceptable salt thereof.

4. A compound of the formula:

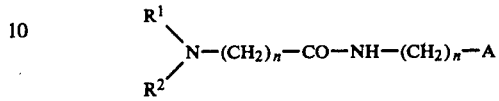

wherein
A is —SO$_2$OH;
R$^1$ is acetyl or benzoyl;
R$^2$ is hydrogen; and
n is 2 or 3; or a pharmaceutically acceptable salt thereof.

5. N-Carbobenzoxy-γ-aminobutyryl-ethanolamine phosphate or a pharmaceutically acceptable salt thereof.

6. N-Carbobenzoxy-γ-aminobutyryl-propanolamine phosphate or a pharmaceutically acceptable salt thereof.

7. N-Carbobenzoxy-β-alanyl-ethanolamine phosphate or a pharmaceutically acceptable salt thereof.

8. N-Carbobenzoxy-β-alanyl-propanolamine phosphate or a pharmaceutically acceptable salt thereof.

9. N-Acetyl-γ-aminobutyryl-taurine or a pharmaceutically acceptable salt thereof.

10. N-Benzoyl-γ-aminobutyryl-taurine or a pharmaceutically acceptable salt thereof.

11. γ-Aminobutyryl-homotaurine or a pharmaceutically acceptable salt thereof.

12. N-Carbobenzoxy-γ-aminobutyryl-homotaurine or a pharmaceutically acceptable salt thereof.

13. β-alanyl-homotaurine or a pharmaceutically acceptable salt thereof.

* * * * *